United States Patent
Richmond et al.

(10) Patent No.: US 12,186,222 B2
(45) Date of Patent: Jan. 7, 2025

(54) ORTHOPEDIC DEVICE HAVING WRAP AND SINGLE STRAP

(71) Applicant: VISION QUEST INDUSTRIES INCORPORATED, Irvine, CA (US)

(72) Inventors: Chelsey M. Richmond, La Mesa, CA (US); David K. Combs, Oceanside, CA (US); David B. Winer, Vista, CA (US); Kevin R. Lunau, La Vernia, TX (US); Carl J. Macchia, San Clemente, CA (US)

(73) Assignee: VISION QUEST INDUSTRIES INCORPORATED, Irvine, CA (US)

( * ) Notice: Subject to any disclaimer, the term of this patent is extended or adjusted under 35 U.S.C. 154(b) by 404 days.

(21) Appl. No.: 17/782,102

(22) PCT Filed: Dec. 4, 2020

(86) PCT No.: PCT/US2020/063434
§ 371 (c)(1),
(2) Date: Jun. 2, 2022

(87) PCT Pub. No.: WO2021/113729
PCT Pub. Date: Jun. 10, 2021

(65) Prior Publication Data
US 2023/0009015 A1    Jan. 12, 2023

Related U.S. Application Data

(60) Provisional application No. 62/943,997, filed on Dec. 5, 2019.

(51) Int. Cl.
*A61F 5/01*    (2006.01)
*A61F 13/06*    (2006.01)

(52) U.S. Cl.
CPC .......... *A61F 5/0123* (2013.01); *A61F 13/062* (2013.01); *A61F 2005/0165* (2013.01); *A61F 2005/0167* (2013.01)

(58) Field of Classification Search
CPC .. A61F 5/0123; A61F 5/00; A61F 5/01; A61F 5/04; A61F 5/0125; A61F 5/0106;
(Continued)

(56) References Cited

U.S. PATENT DOCUMENTS 3,204,307 A    9/1965    Dunn
4,005,506 A    2/1977    Moore
(Continued)

FOREIGN PATENT DOCUMENTS

DE    102015100628 A1    7/2015
EP    1276948 A1    1/2003
(Continued)

OTHER PUBLICATIONS

International Application No. PCT/US20/63434, International Search Report and the Written Opinion of the International Searching Authority, or the Declaration Dated Feb. 24, 2021 (7 Pages).
(Continued)

*Primary Examiner* — Alireza Nia
*Assistant Examiner* — Daniel A Miller
(74) *Attorney, Agent, or Firm* — Lawrence N. Ginsberg

(57) ABSTRACT

The orthopedic device includes an articulating frame including a thigh portion including a curved thigh cuff, a calf portion including a curved calf cuff, and a center hinge connecting the thigh portion and the calf portion. A strap includes a calf end segment securely attachable to the calf portion. A suspension segment is adjacent to the calf end segment. A thigh end segment is securely attachable to the thigh portion. A spiraling segment is adjacent to the thigh end segment. An intermediate segment formed of webbing
(Continued)

material is between the suspension segment and the spiraling segment. The clip engages the intermediate segment. The clip is engageable with a clip receptacle positioned on the calf portion. During use, the suspension segment lays across the top part of the calf minimizing migration. The intermediate segment facilitates movement of the strap through the clip adjusting the spiraling segment and the suspension segment.

14 Claims, 11 Drawing Sheets

(58) Field of Classification Search
CPC ........ A61F 5/0109; A61F 5/0102; A61F 5/05; A61F 5/013; A61F 5/37; A61F 2005/0165; A61F 2005/0167; A61F 2005/0137; A61F 2005/0179; A61F 2005/0139; A61F 2005/0146; A61F 2005/0197; A61F 2005/0172; A61F 2005/0158; A61F 2005/0169; A61F 2005/0181; A61F 2005/0174; A61F 13/062; A61F 2/3886; E05D 11/0054; E05D 7/0054; E05D 3/06; A44B 11/008; A44B 11/04; A44B 11/006; A44B 11/2507; A44B 11/2511; A44B 11/2561; A44B 11/2592
USPC .......................................................... 602/26
See application file for complete search history.

(56) References Cited

U.S. PATENT DOCUMENTS

| | | | |
|---|---|---|---|
| 4,176,840 A | 12/1979 | Lanning |
| 4,726,362 A | 2/1988 | Nelson |
| 4,830,413 A | 5/1989 | Bisbing |
| 5,226,875 A | 7/1993 | Johnson |
| 5,277,698 A | 1/1994 | Taylor |
| 5,356,370 A | 10/1994 | Fleming |
| 5,662,596 A | 9/1997 | Young |
| 5,836,902 A | 11/1998 | Gray |
| 5,857,989 A | 1/1999 | Smith |
| D473,654 S | 4/2003 | Iglesias et al. |
| 6,540,709 B1 | 4/2003 | Smits |
| 6,971,996 B2 | 12/2005 | Houser |
| D527,825 S | 9/2006 | Ingimundarson et al. |
| D529,150 S | 9/2006 | Ingimundarson |
| D529,180 S | 9/2006 | Ingimundarson et al. |
| 7,117,569 B2 | 10/2006 | Bledsoe |
| 7,122,016 B1 | 10/2006 | DeToro et al. |
| 7,198,610 B2 | 4/2007 | Ingimundarson et al. |
| 7,201,728 B2 | 4/2007 | Sterling |
| D558,884 S | 1/2008 | Ingimundarson et al. |
| 7,346,965 B2 | 3/2008 | Hsiao |
| D577,828 S | 9/2008 | Ingimundarson et al. |
| 7,481,785 B2 | 1/2009 | Turrini et al. |
| 7,500,957 B2 | 3/2009 | Bledsoe |
| 7,662,122 B2 | 2/2010 | Sterling |
| 7,758,527 B2 | 7/2010 | Gilmour et al. |
| 7,867,183 B2 | 1/2011 | Kazmierczak et al. |
| D639,441 S | 6/2011 | Sferle |
| D665,950 S | 8/2012 | Rokitta |
| 8,241,234 B2 | 8/2012 | Ingimundarson et al. |
| 8,257,293 B2 | 9/2012 | Ingimundarson et al. |
| 8,740,829 B2 | 6/2014 | Lee et al. |
| 8,911,389 B2 | 12/2014 | Reinhardt et al. |
| D733,894 S | 7/2015 | Ortega |
| D735,872 S | 8/2015 | Ljubimir et al. |
| D744,111 S | 11/2015 | Dunn et al. |
| 9,220,622 B2 | 12/2015 | Ingimundarson et al. |
| 9,500,957 B2 | 11/2016 | Hartjes |
| D779,076 S | 2/2017 | Chang et al. |
| D779,078 S | 2/2017 | Drewitz et al. |
| D804,044 S | 11/2017 | Savarad |
| D810,309 S | 2/2018 | Forbes et al. |
| D820,991 S | 6/2018 | Hylton et al. |
| D825,767 S | 8/2018 | Kruchem |
| 10,052,221 B2 | 8/2018 | Albertsson et al. |
| D834,204 S | 11/2018 | Chang et al. |
| D835,289 S | 12/2018 | Frost |
| D844,794 S | 4/2019 | Mitchell |
| D846,130 S | 4/2019 | Watabe et al. |
| 2004/0267179 A1 | 12/2004 | Lerman |
| 2007/0077832 A1 | 4/2007 | Godoy |
| 2007/0213648 A1 | 9/2007 | Ferrigolo et al. |
| 2009/0287128 A1 | 11/2009 | Ingimundarson et al. |
| 2010/0008197 A1 | 4/2010 | Ingimundarson et al. |
| 2010/0174221 A1 | 7/2010 | Ingimundarson et al. |
| 2012/0165713 A1 | 6/2012 | Forbes et al. |
| 2013/0178772 A1 | 7/2013 | Oaks et al. |
| 2013/0296757 A1* | 11/2013 | Kaphingst ............... A61F 5/013 602/20 |
| 2014/0194801 A1 | 7/2014 | Thorsteinsdottir et al. |
| 2014/0214016 A1 | 7/2014 | Ingimundarson et al. |
| 2014/0276301 A1 | 9/2014 | Grim et al. |
| 2014/0364782 A1 | 12/2014 | Knecht |
| 2015/0005685 A1 | 1/2015 | Chetlapalli et al. |
| 2015/0108191 A1 | 4/2015 | Velarde |
| 2015/0173927 A1 | 6/2015 | Castillo |
| 2015/0305908 A1 | 10/2015 | Spade |
| 2016/0113803 A1 | 4/2016 | Mitchell |
| 2016/0193066 A1 | 7/2016 | Albertsson et al. |
| 2016/0302955 A1 | 10/2016 | Siddiqui et al. |
| 2017/0252200 A1 | 9/2017 | Taylor |
| 2017/0281390 A1 | 10/2017 | Abdul-Hafiz et al. |
| 2017/0354527 A1 | 12/2017 | Schwark |
| 2018/0042754 A1 | 2/2018 | Ingimundarson et al. |
| 2019/0105188 A1 | 4/2019 | Petursson et al. |
| 2019/0117428 A1 | 4/2019 | Sigurdsson et al. |
| 2019/0117429 A1 | 4/2019 | Wang |
| 2019/0117430 A1 | 4/2019 | Bonutti et al. |
| 2019/0290465 A1 | 9/2019 | Fleming |

FOREIGN PATENT DOCUMENTS

| | | |
|---|---|---|
| EP | 127694 A4 | 4/2010 |
| EP | 1276948 B1 | 10/2011 |
| WO | 201088716 A1 | 8/2010 |

OTHER PUBLICATIONS

International Application No. PCT/US20/63432, International Search Report and the Written Opinion of the International Searching Authority, or the Declaration Dated Apr. 2, 2021 (12 Pages).
International Application No. PCT/US20/63032, International Search Report and the Written Opinion of the International Searching Authority, or the Declaration Dated Mar. 2, 2021 (11 Pages).

* cited by examiner

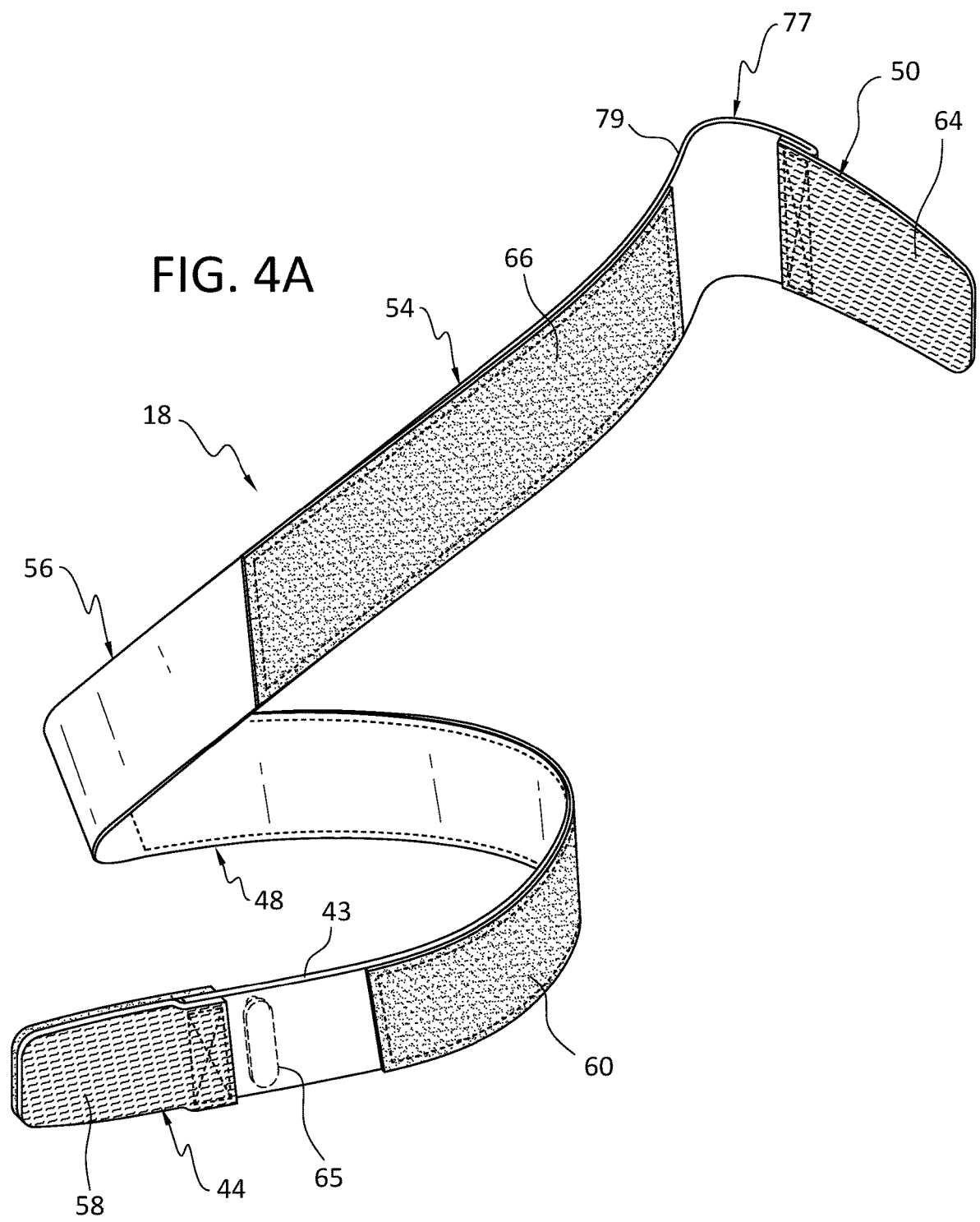

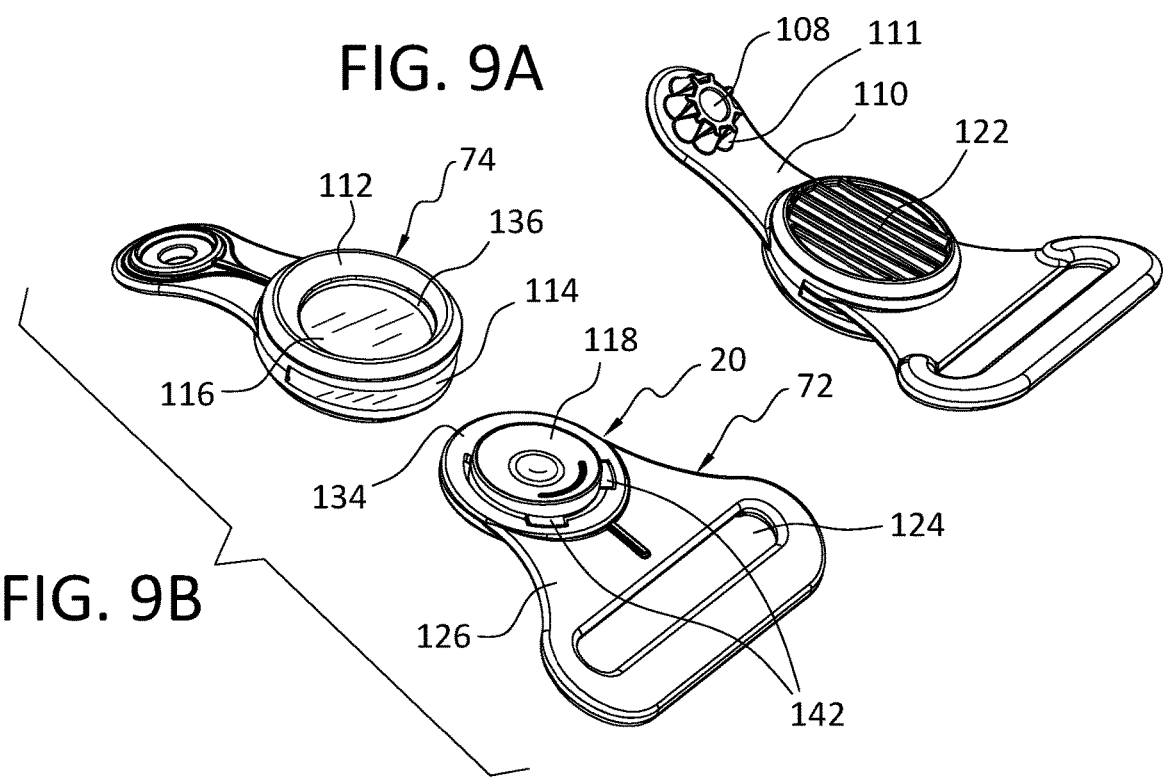
FIG. 9A
FIG. 9B
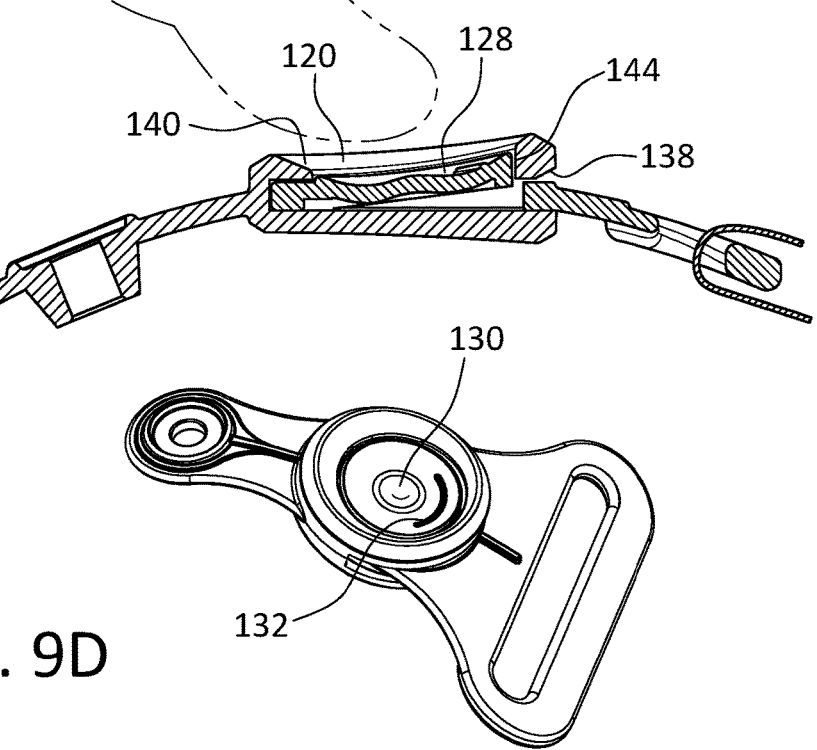
FIG. 9C
FIG. 9D

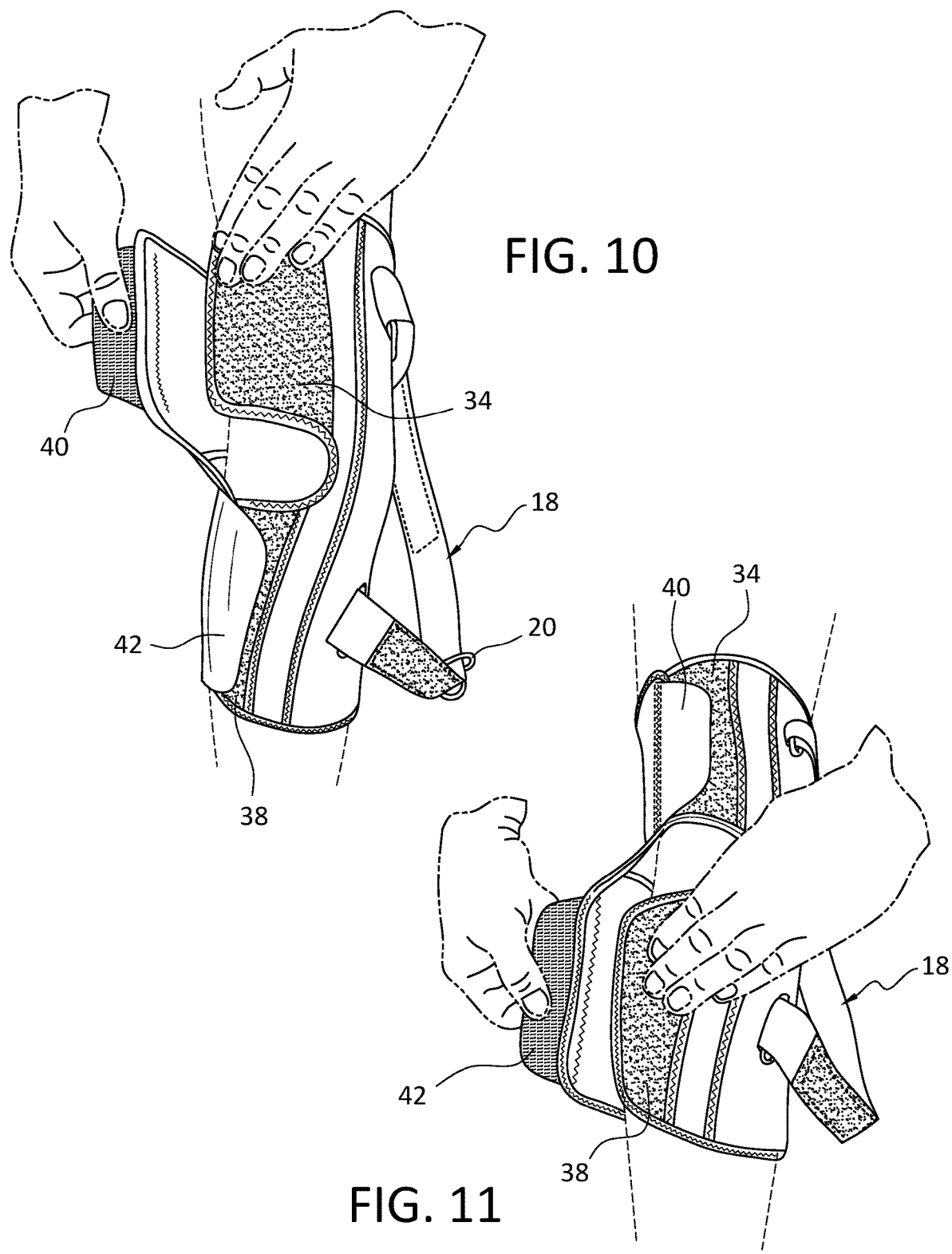

ORTHOPEDIC DEVICE HAVING WRAP AND SINGLE STRAP

CROSS REFERENCE TO RELATED APPLICATIONS

This patent application claims the benefit of U.S. Provisional Application No. 62/943,997 filed Dec. 5, 2019. The entire content of Application No. 62/943,997 is incorporated by reference herein.

BACKGROUND OF THE INVENTION

1. Field of the Invention

The present invention relates generally to the field of orthopedic supports and braces, and more particularly to a knee wrap brace with improvements in more intuitive donning, doffing and comfort.

2. Description of the Related Art

Osteoarthritis in the knee occurs when the cartilage that cushions the ends of bones in your knee gradually deteriorates. Joint issues that present themselves may include swelling, tenderness, reduced range of motion, instability, and change in gait. Load distribution is most often altered as the affected compartment deteriorates over time. This unbalanced loading can generate increased pressure of bone on bone contact which results in knee pain during the load bearing phase of the gait. As will be disclosed below, the present invention addresses the unbalanced loading on the medial or lateral compartment of the joint.

Knee bracing is useful to provide compartment pain relief by reducing the load on the affected compartment. Rigid braces provide great benefits but are often bulky and uncomfortable over long periods of wear. These conditions reduce patient compliance and treatment becomes less effective. As will be disclosed below, the present wrap brace provides greater comfort and less bulk than rigid braces while still providing pain relief over longer periods. The elastic wrap is easy to don and generates suitable joint compression and stability. Rigid knee bracing is useful in pain, relief, restoring, and extending daily activities. While these types of knee braces are successful at stabilizing a knee and reducing pain, users may find these configurations to be bulky, difficult to don, and uncomfortable to wear. As will be disclosed below, the present wrapping brace with a spiral strap offers similar benefits of knee stabilization and unloading in a more comfortable, easy to don style, thereby extending compliance and treatment. A patent disclosing a soft type brace is U.S. Pat. No. 10,052,221 entitled "Orthopedic Device for Treating Osteoarthritis of the Knee."

Various types of orthopedic devices are disclosed in U.S. application Ser. No. 14/989,528 entitled "Orthopedic Device for Treating Osteoarthritis of the Knee"; U.S. application Ser. No. 14/169,786 entitled "Orthopedic Device Having Detachable Components for Treatment Stages and Method for Using the Same"; U.S. application Ser. No. 14/148,881 entitled "Orthopedic Device and Method for Securing the Same"; U.S. application Ser. No. 12/728,336 entitled "Knee Brace and Method for Securing the Same"; U.S. application Ser. No. 12/631,057 entitled "Knee Brace and Method for Securing the Same"; U.S. Pat. No. 7,198,610 entitled "Knee Brace and Method for Securing the Same".

SUMMARY OF THE INVENTION

In one aspect, the orthopedic device includes a wrap, an articulating frame housed within the wrap, a strap attached to the frame, and a clip. The articulating frame includes a thigh portion including a semi-flexible curved thigh cuff, a calf portion including a semi-flexible curved calf cuff, and a center hinge connecting the thigh portion and said calf portion. The strap includes a calf end segment securely attachable to the calf portion of the articulating frame. A suspension segment is adjacent to the calf end segment. A thigh end segment is securely attachable to the thigh portion of the articulating frame. A spiraling segment is adjacent to the thigh end segment. An intermediate segment is between the suspension segment and the spiraling segment. The intermediate segment is formed of webbing material. The clip includes a D-ring portion for engaging the intermediate segment. The clip is engageable with a clip receptacle positioned on the calf portion of the articulating frame. During use, the suspension segment lays across the top part of the calf muscle to provide vertical support to minimize migration of the device. The intermediate segment facilitates movement of the strap through the D-ring portion to provide adjustment of the spiraling segment and the suspension segment.

Thus, the helical annular force strap secured around the wrap provides additional compression and stabilization during leg extension in the load bearing phase of the gait. The routing nature of this single strap also affords an anti-migration quality during use. Metal uprights and other configurations within the articulating frame benefit the user by providing proportional spring-back during the gait phase.

The semi-flexible curved thigh cuff preferably has a teardrop shape; and the semi-flexible curved calf cuff has an upside-down teardrop shape.

The orthopedic device includes a thigh portion with an upright thigh bar having an upright thigh bar first end and an upright thigh bar second end. The upright thigh bar first end is connected to the hinge. The semi-flexible curved thigh cuff extends from the upright thigh bar second end. Similarly, the calf portion includes an upright calf bar having an upright calf bar first end and an upright calf bar second end. The upright calf bar first end is connected to the center hinge.

The clip includes a pushbutton portion; and, the calf cuff includes a pivotal pushbutton receptacle secured thereto that provide easy fastening.

In another aspect, the present invention is embodied as a method for donning an orthopedic device. The method of donning the orthopedic device includes first providing the orthopedic device including a wrap; an articulating frame; a strap attached to the frame; and, a clip. The articulating frame is housed within the wrap and includes a thigh portion, a calf portion, and a center hinge. The thigh portion includes a semi-flexible curved thigh cuff. The calf portion includes a semi-flexible curved calf cuff. The center hinge connects the thigh portion and the calf portion.

The strap includes a calf end segment securely attachable to the calf portion of the articulating frame. A suspension segment is adjacent to the calf end segment. A thigh end segment is securely attachable to the thigh portion of the articulating frame. A spiraling segment is adjacent to the thigh end segment. An intermediate segment is between the suspension segment and the spiraling segment. The intermediate segment is formed of webbing material. The clip includes a D-ring portion for engaging the intermediate segment. The clip is engageable with a clip receptacle positioned on the calf portion of the articulating frame.

In this method of donning the orthopedic device the wrap is placed around the leg of the user. The strap is wrapped from the side of the leg, across the front of the leg, continuing posteriorly across the upper portion of the calf, wherein the spiraling segment begins at the calf and spirals posteriorly and ends anteriorly at the thigh.

The clip is engaged into the clip receptacle. The strap tension is adjusted at the thigh end segment.

BRIEF DESCRIPTION OF THE DRAWINGS

FIG. 4A is a perspective view of the strap of the orthopedic device.

FIG. 9A is a perspective view of the underside of the pushbutton clip of the present invention.

FIG. 9B is a top view of the pushbutton clip and the pushbutton receptacle shown detached.

FIG. 9C is a section view taken along line 9C-9C of FIG. 1, showing the user's finger detaching the pushbutton clip from the pushbutton receptacle.

FIG. 9D is a top view of the pushbutton clip and the pushbutton receptacle shown attached.

FIG. 10 illustrates use of the thigh fastening tab attaching to the front thigh closure at the thigh end of the orthopedic device.

FIG. 11 illustrates use of the calf fastening tab attaching to the front calf closure at the calf end of the orthopedic device.

DETAILED DESCRIPTION OF THE INVENTION

Figures 1, 2:
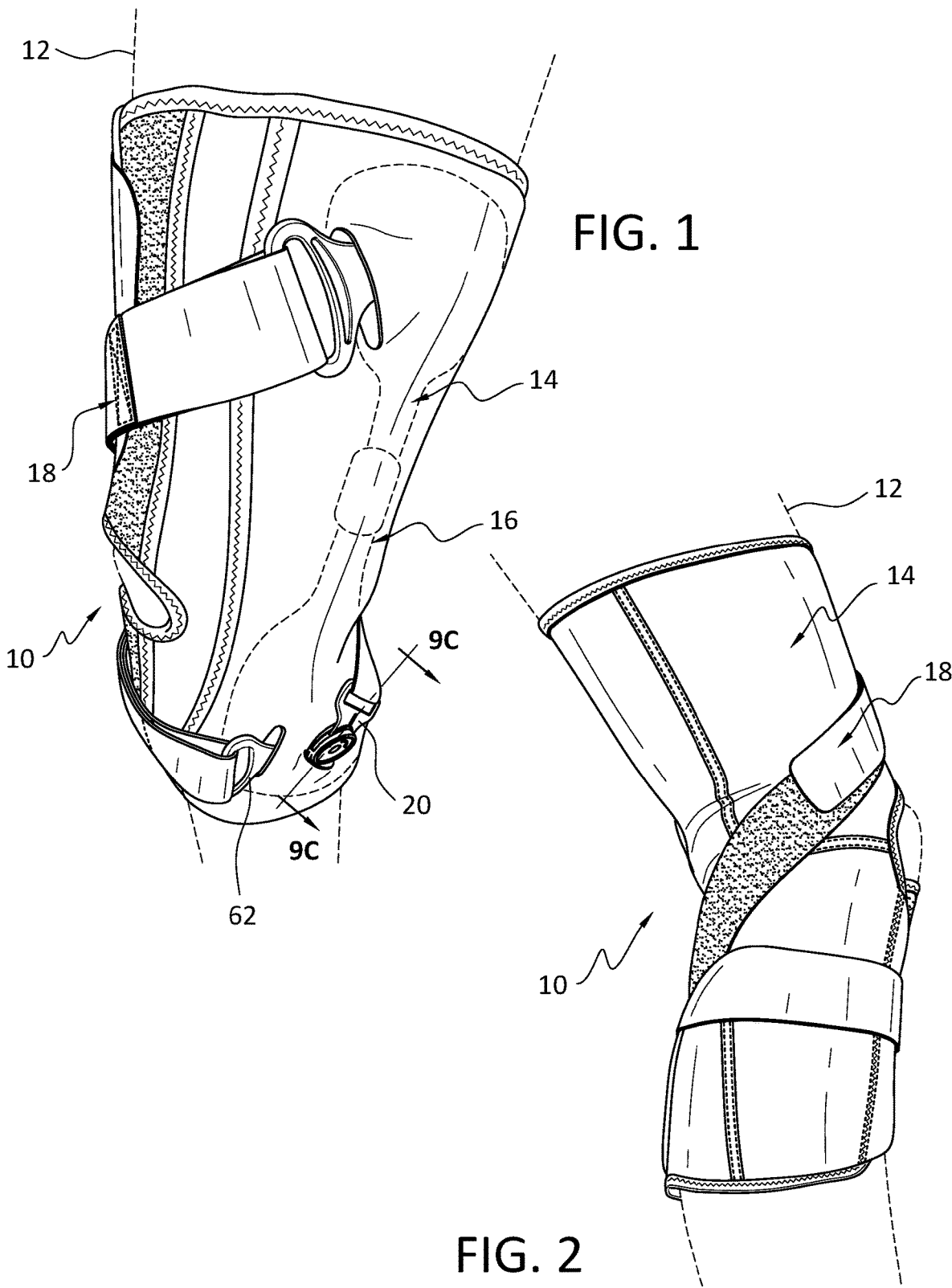
FIG. 1 is a front, left side perspective view of the orthopedic device of the present invention shown on the leg of a user.
FIG. 2 is a rear, right side perspective view of the orthopedic device of FIG. 1.
Figure 3:
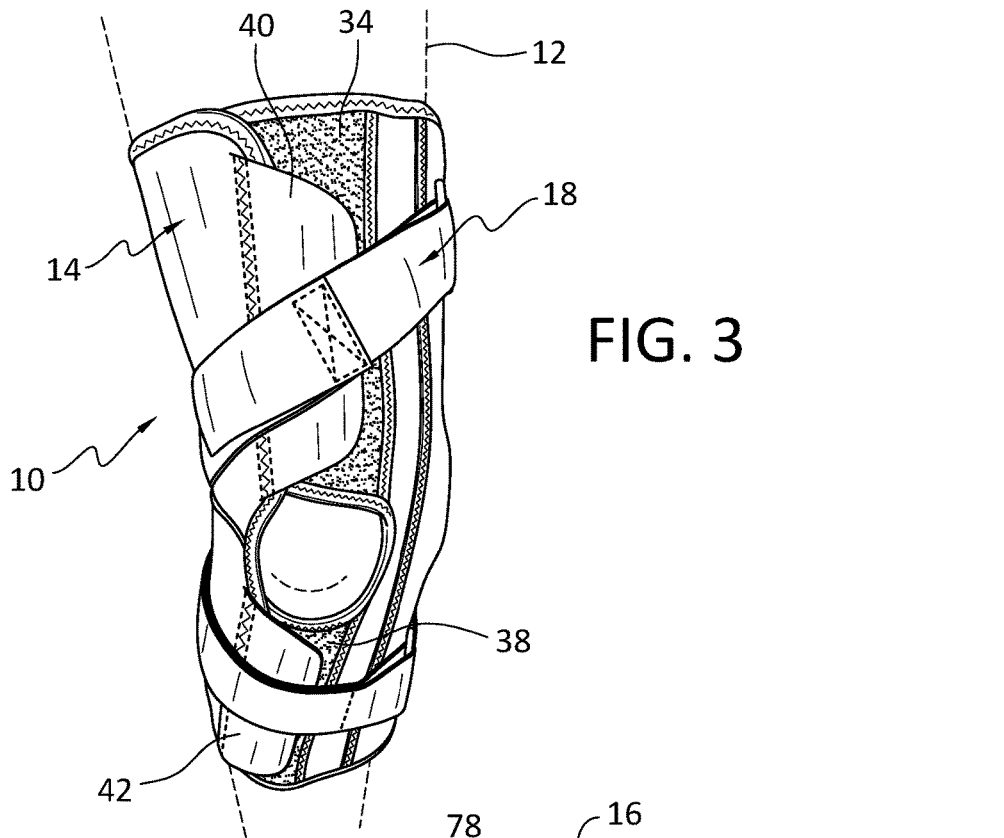
FIG. 3 is a front perspective view of the orthopedic device of FIG. 1.

Referring now to the drawings and the characters of reference marked thereon, FIGS. 1-4 illustrate a preferred embodiment of the orthopedic device of the present invention, designated generally as 10, shown positioned on the leg of the user, shown in phantom lines 12. The orthopedic device 10 includes a wrap, designated generally as 14, an articulating frame designated generally as 16 (in phantom), a strap designated generally as 18, and a clip designated generally as 20.

Figure 4:
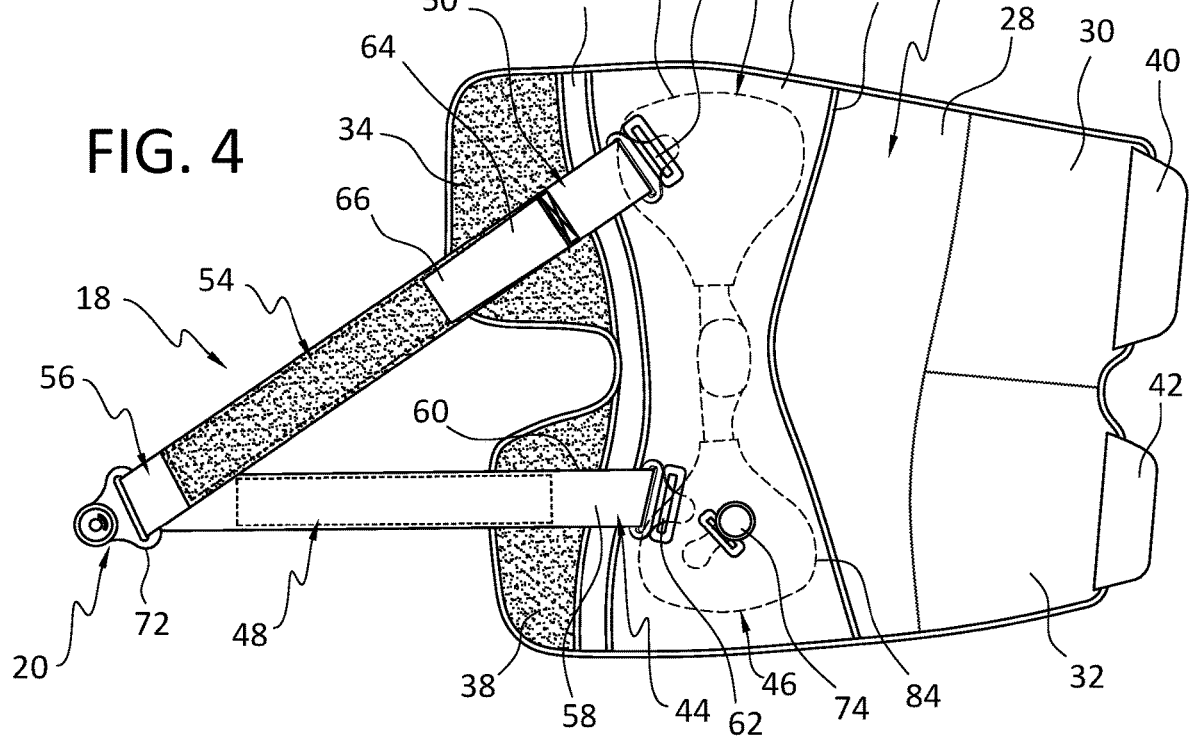
FIG. 4 is a perspective view of the orthopedic device unstrapped on a level surface.

As can be best seen in FIG. 4, the wrap 14 includes multiple panels designed to contour to the leg and means to secure to itself creating a sleeve structure. The wrap 14 includes a main panel, designated generally as 22. The main panel includes two layers, an inner layer and a thicker outer layer. The main panel is sewn along three sides, creating a pocket for the articulating frame 16. The open end can be sealed with a strip of loop engageable hook along seam 26. A posterior panel 24 is secured to a first end of the main panel 22 by a posterior seam (i.e. stich) 26. The posterior panel 24 includes three pieces 28, 30, 32 for shaping the device to the user's anatomy. A front thigh closure 34 is connected to a second end of the main panel (by an anterior seam 36). The front thigh closure 34 includes a thigh loop surface. A front calf closure 38 is connected to the second end of the main panel (by the anterior seam 36). The front calf closure 38 includes a calf loop surface. A thigh fastening tab 40 extends from the posterior panel 24 which includes a thigh hook material. A calf fastening tab 42 extends from the posterior panel 24 which includes a calf hook material.

Functionally, the strap 18 can be defined in terms of segments and sub-segments. As can best be seen in FIGS. 4 and 4A, the strap 18 includes a calf end segment 44. The calf end segment 44 is securely attachable to a calf portion 46 of the articulating frame 16. (The calf portion 46 of the articulating frame 16 can best seen in FIGS. 4 and 5.) A suspension segment 48 is adjacent to the calf end segment 44. A thigh end segment 50 is securely attachable to a thigh portion 52 (best seen in FIGS. 5 and 6) of the articulating frame 16. A spiraling segment 54 is adjacent to the thigh end segment 50. An intermediate segment 56 is between the suspension segment 48 and the spiraling segment 54.

The calf portion 46 of the articulating frame 16 includes a calf D-ring 62 configured to adjustably engage the calf hook sub-segment 58 and the calf loop sub-segment 60. Similarly, the thigh end segment 50 comprises a thigh hook sub-segment 64 adjacent a thigh loop sub-segment 66. The thigh portion 52 of the articulating frame 16 includes a thigh D-ring 68 configured to adjustably engage the thigh hook sub-segment 64 and the thigh loop sub-segment 66.

As will be further described below, during use the suspension segment 48 lays across the top part of the calf muscle to provide vertical support to minimize migration of the orthopedic device 10. The intermediate segment 56 facilitates movement of the strap 18 through a D-ring portion 72 of a clip 20 to provide adjustment of the spiraling segment 54 and the suspension segment 48.

Figure 7:
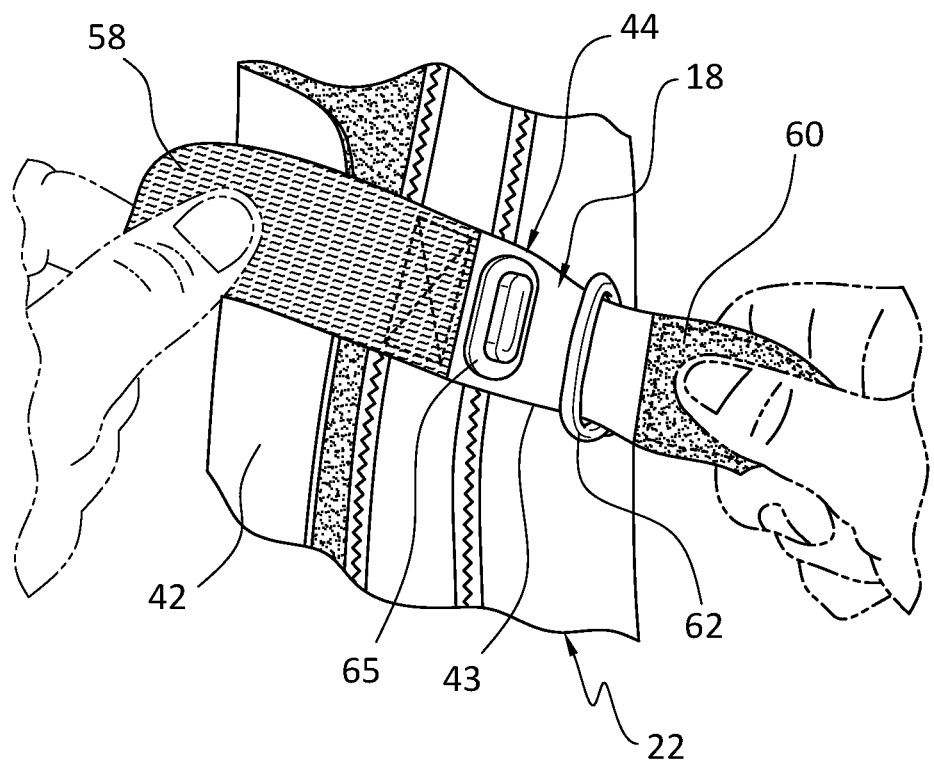
FIG. 7 is a side perspective view of a portion of the orthopedic device, showing the strap attachment at the calf end of the main panel of the orthopedic device.

As best seen in FIGS. 4A and 7, the strap 18 includes a strap stopper 65 sewn onto the strap 18 at one end of the suspension segment 48 and adjacent to the calf hook sub-segment 58. The strap stopper 65 comprises raised material. Another stopping portion 67 at the thigh end segment 50 comprises build up material to encourage strap retention.

The hook and loop type fasteners may be of the type trademarked as VELCRO® or similar hook and loop fasteners manufactured by Paiho North America. In a preferred embodiment, the strap 18 has one continuous substrate 77 of webbing material other than the two hook sub-segments 58, 64. The two loop sub-segments 60, 66 are comprised of loop strips (patches) sewn onto the continuous substrate of webbing material. The intermediate segment 56 is formed of the bare substrate of webbing material which provides easy sliding. This webbing material is preferably nylon. The thigh hook sub-segment 64 may be formed of a laminate of molded vinyl and hook material. The calf hook sub-segment 60 may be formed of a laminate of molded nylon hook material over loop material.

In the embodiment shown the thigh loop sub-segment 66 comprises a substantial portion of the spiraling segment 54. Also, the calf loop sub-segment 60 comprises a substantial portion of the suspension segment 48. However, it is understood that these sub-segments 60, 66 may have different lengths as long as they are sufficiently long to engage their respective hook sub-segments.

The clip 20 includes the D-ring portion 72 for engaging the intermediate segment 56. The clip 20 is engageable with a clip receptacle 74 positioned on the calf portion 46 of the articulating frame 16. In a preferred embodiment and as shown the D-ring portion 72 has a rectangular opening 74 that minimizes bunching and provides lubricious movement of the strap.

Figure 5:
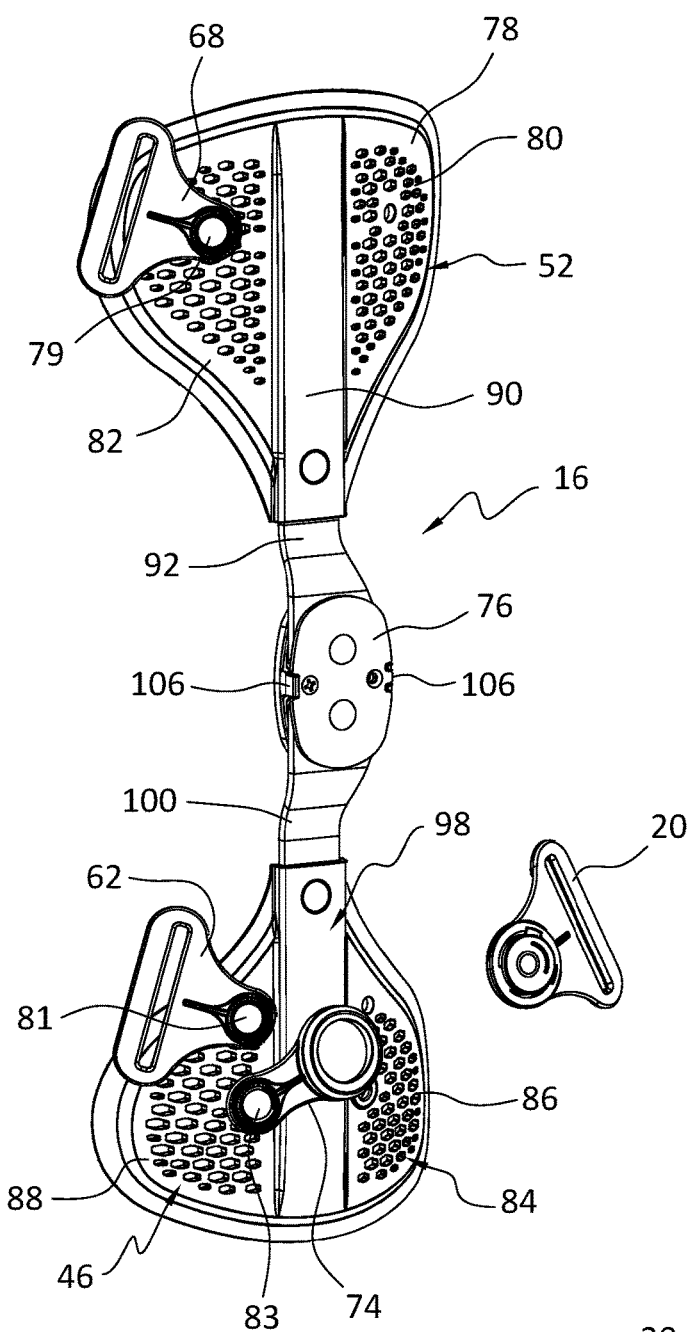
FIG. 5 is a front, side perspective view of the articulating frame of the orthopedic device.
Figure 6:
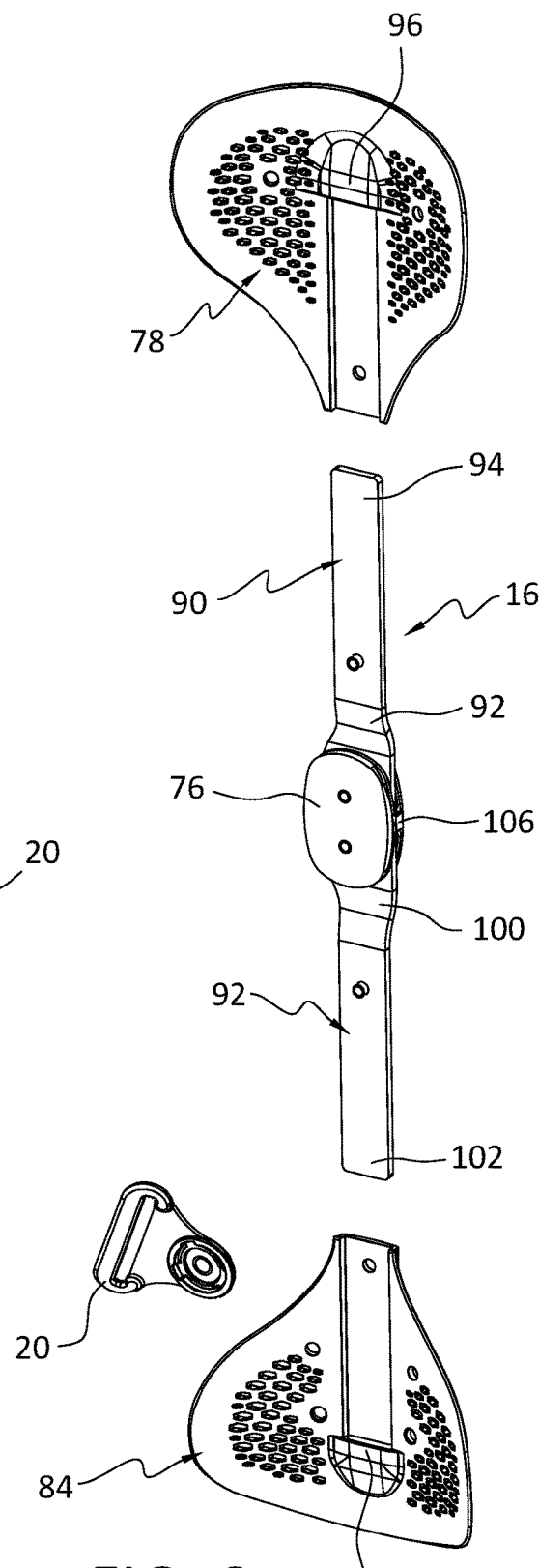
FIG. 6 is a rear, side perspective view of the articulating frame of the orthopedic device.

Referring now to FIGS. 5-6, the articulating frame 16 includes a thigh portion 52, a calf portion 46 and a center hinge 76. The thigh portion 52 includes a semi-flexible curved thigh cuff 78 with a first thigh side 80 and a second thigh side 82. The first thigh side 80 and the second thigh side 82 are symmetrical about a central axis and are configured to wrap partially anteriorly and partially posteriorly to the leg. Similarly, the calf portion 46 includes a semi-flexible curved calf cuff 84 with a first calf side 86 and a second calf side 88. The first calf side 86 and the second calf side 88 are symmetrical about a central axis configured to wrap partially anteriorly and partially posteriorly to the leg. The center hinge 76 connects the thigh portion 52 and the calf portion 46.

The semi-flexible curved thigh cuff 78 has a teardrop shape. The semi-flexible curved calf cuff 84 has an upside-down teardrop shape. Such a teardrop shape is defined by a series of positive curves from a wide end inflecting to a negative curve approaching a narrow end. As can be seen in this figure, to further enhance flexibility of the cuff, the thicknesses of the cuffs around the perimeter have been thinned out. This helps the cuffs conform to the leg and minimizes the cuff edges from "digging" into the user. The term "semi-flexible" as used herein relative to each cuff refers to the ability of each cuff to conform to the curvature profile of the user's leg. Each cuff is preferably formed of a polyester elastomer plastic approximately 3 mm thick. An example material that can be used is sold by Dupont under the trademark Hytrel® 7246 which is a high modulus grade with nominal hardness of 72D.

The thigh D-ring 68 is rotatably connected to the thigh cuff 78 by, for example, a rivet 79. Similarly, the calf D-ring 62 is rotatably connected to the calf cuff 84 by, for example, a rivet 81. A calf receptacle 74 is rotatably connected to the calf cuff 84 by, for example, a rivet 83. Other suitable rotatable fastening means could be utilized other than the rivets discussed about for these items.

The thigh portion 52 includes an upright thigh bar 90 having an upright thigh bar first end 92 and an upright thigh bar second end 94. The upright thigh bar first end 92 is connected to the center hinge 76. The semi-flexible curved thigh cuff 78 includes a thigh cuff pocket 96 for securing the upright thigh bar second end 94 therewithin.

The calf portion 46 includes an upright calf bar 98 having an upright calf bar first end 100 and an upright calf bar second end 102. The upright calf bar first end 100 is connected to the center hinge 76. The semi-flexible curved calf cuff 84 includes a calf cuff pocket 104 for securing the upright calf bar second end 102 therewithin. The pockets 96, 104 provide the capability of the upright thigh bar 90 and upright calf bar 92 to be secured using only one rivet apiece.

As noted above, the center hinge 76 is configured to connect the upright thigh bar 90 and the upright calf bar 98.

The collective nature of this metal portion of the articulating frame 16 provides spring properties that apply an unloading pull-force in the transverse plane. This cooperates with the helical nature of the strap to provide annular compression to the leg and subsequent knee stability during the leg extension phase of the gait. The center hinge 76 includes inserts 106 at each side for limiting flexion and extension. The center hinge 76 shown is a polycentric hinge; however, a monocentric hinge can be substituted.

The components of the articulating frame 16 are designed to create left and right leg configurations. This is a result of symmetry of the cuffs 78 and 84 designed to receive either the upright thigh bar 90 and/or the upright calf bar 92.

Referring now to FIG. 7, the strap 18 is shown being anchored at the calf portion 46 of the frame 16 via the calf D-ring 62. The calf end segment 44 includes the calf hook sub-segment 58 spaced from a calf loop sub-segment 60. Substrate webbing 77 includes a substrate sub-segment 43 located between the calf hook sub-segment 58 and the calf loop sub-segment 60. The strap stopper 65 is located on the webbing sub-segment 43.

Figure 8:
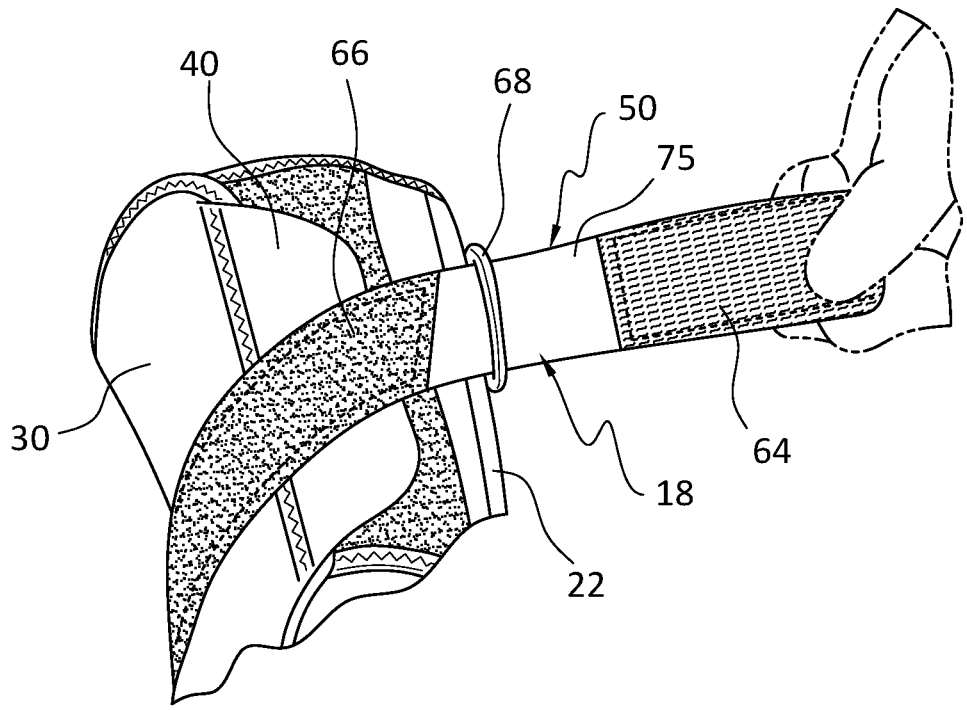
FIG. 8 is a perspective view of a portion of the orthopedic device, showing the strap attachment at the thigh end of the main panel of the orthopedic device.

Referring now to FIG. 8, the strap 18 is shown being anchored at the thigh portion 52 of the frame 16 via the calf D-ring 68. The thigh end segment 50 includes the thigh hook sub-segment 64 spaced from a thigh loop sub-segment 66. Substrate webbing 77 includes a substrate sub-segment 75 located between the thigh hook sub-segment 64 and the thigh loop sub-segment 66.

Referring now to FIGS. 9A-9D, the pushbutton clip 20 and pushbutton receptacle 74 provide quick attachment or release of the strap 18 from the articulating frame 16 for donning and doffing. The pushbutton assembly is illustrated, which collectively includes the receiver component (i.e. receptacle 74) that gets riveted to the calf cuff 84 and a pushbutton clip 20 (i.e. chafe) that attaches to the strap 18. The receptacle 57 has a hole 108 for the rivet to attach it to the brace (the articulating frame 16) which it can rotate on, a thin area of plastic 110 between the rivet area and a push button area 112 that allows the receiver to flex in order to match the circumference of the anatomy. The area around the rivet hole includes a boss (raised rim) 111 for clearance. The push button area 112 has a slot 114 for the pushbutton clip to slide into, a hole 116 for a button 118 to snap into and retain the chafe 20 plus a dished-out area 120 that allows the finger to easily navigate to the button that also helps prevent accidental pressing of the button. The bottom side of the slot has a ribbed exterior section 122 to keep the bottom from flexing too much that the button cannot accidentally disengage. The pushbutton clip has a slot 124 (in the D-ring portion 72) for the strap to attach through, a thin area of plastic 126 between the slot 124 and the button 118 that allows the pushbutton clip to flex in order to match the circumference of the anatomy. The button 118 has a round shape that allows the pushbutton clip to rotate so that the strap can follow the shape of the anatomy. The concave button 118 in the middle of this round shape has a dished out area 128 that helps prevent accidental pressings which is also more intimate with the shape of the finger that allows for easier pressing. There is a dome 130 in the middle of this dish and a concentric ridge 132 on the exit side that helps the finger get a good grip to activate the button. This button has a flexible hinge area 134 that allows the button 118 to flex out of the way of the receiver hole's wall 136 for removal. The receiver hole's wall 136 has a lead-in chamfer 138 on the upper outside edge created by the slot opening 114. The chamfer 138 assists an entry side 140 of the button 118 through slot 114. It also has two stops 142 that allows the button to not get flexed up into the receiver's hole 136 too far so that the flexible hinge 134 does not get sprung. The height of the button 118 is lower on the entry side 140 so that it is easy to insert but is higher on an exit side 144 for retention. This graded height also flexes the receiver's top section with the hole 136 to slightly flex out of the way for insertion. The entry side 140 is still high enough that the button 118 doesn't accidently disengage itself when the pushbutton clip is rotated while in the receiver. The exit side 144 is high enough for retention, but still can slide through the slot opening 114 of the receiver when being activated. The location of the hinge 134 and stops 142 along with the exit side of the button 144 allows the button to flex up to remain intimate with the receiver's hole 136 wall when being flexed around the anatomy and when stronger forces are being applied from the strap so that the pushbutton clip does not get pulled out of the receiver (receptacle).

Referring now to FIG. 10, during donning the user, with one hand, engages the thigh fastening tab 40 at the front thigh closure 34. The two are pressed together.

Similarly, as shown in FIG. 11, the calf fastening tab 42, and the front calf closure 38 are engaged by the user at the calf. The two are pressed together.

Figure 12:
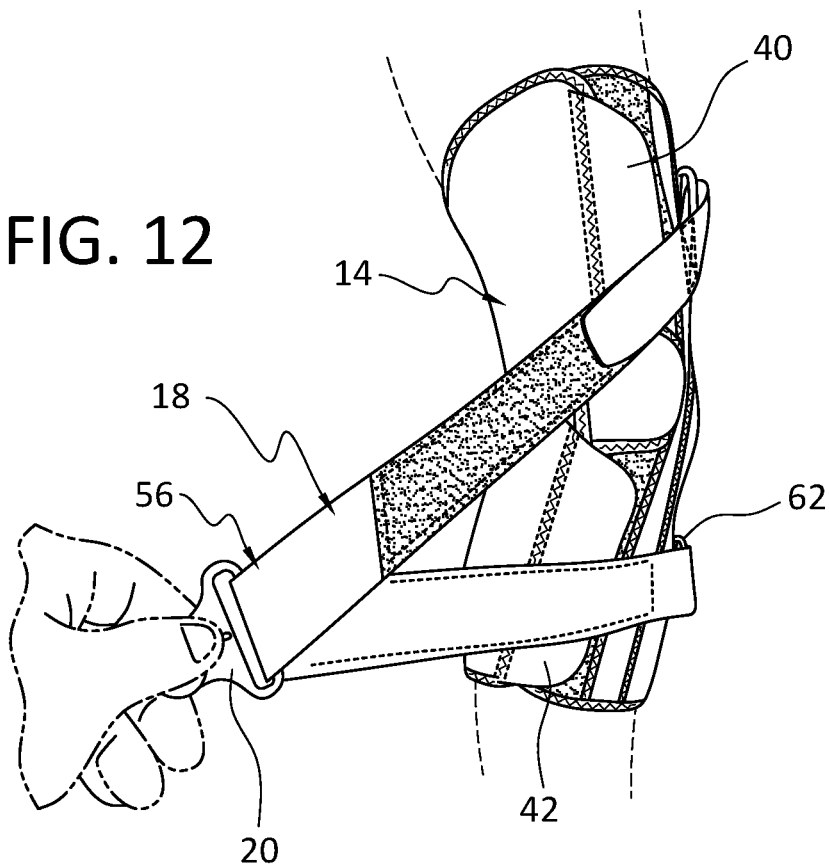
FIG. 12 shows the strap wrapping around the front of the orthopedic device.
Figure 13:
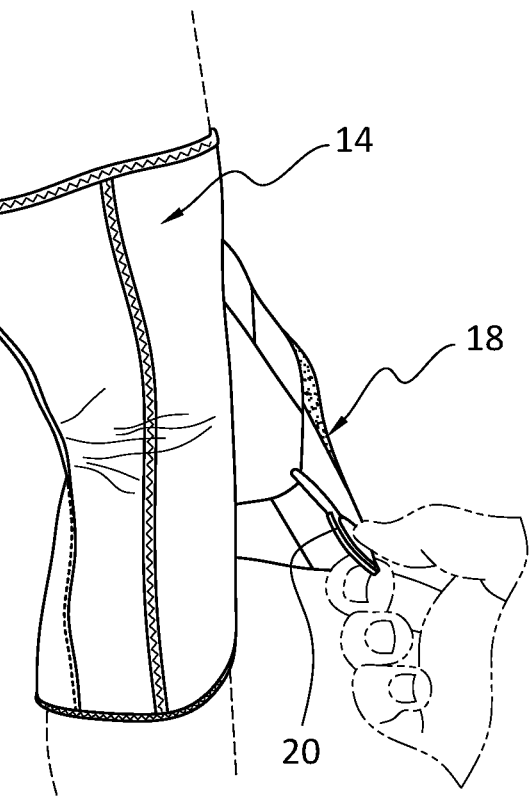
FIG. 13 shows the strap about to be wrapped around the rear of the orthopedic device.
Figure 14:
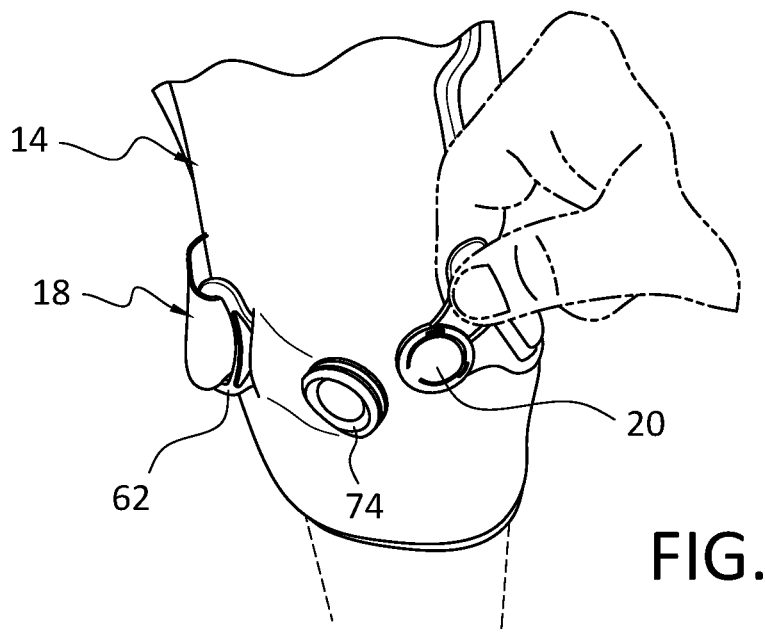
FIG. 14 shows the pushbutton clip connecting to the pushbutton receptacle.

Referring now to FIGS. 12-14, the strap 18 wraps over and across the front of the leg. The strap 18 continues posteriorly and across the upper portion of the calf. The push button clip 20 at the intermediate segment 56 of the strap 18 engages the push button receptacle 74.

Figure 15:
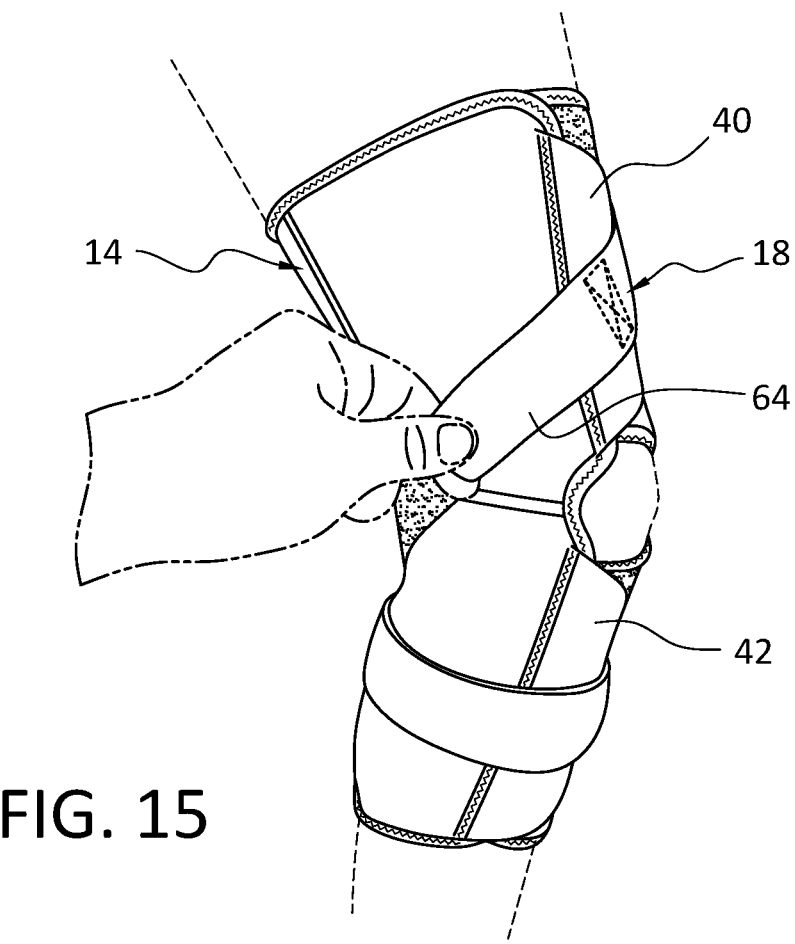
FIG. 15 illustrates adjustment of the strap at the thigh end of the orthopedic device.

Referring now to FIGS. 15, The tension of the strap 18 can be adjusted by the thigh hook sub-segment 64 that provides adjustment to the strap length, as discussed above.

Thus, the spiraling segment 54 provides a helical annular force that is applied around the wrap, which provides additional compression and stabilization during leg extension in the load bearing phase of the gait. The routing nature of this single strap also affords an anti-migration quality during use. The suspension segment 48 lays across the top part of the calf muscle preventing vertical downward migration. As discussed above, the metal uprights and other configurations within the articulating frame benefits the user by providing proportional spring-back during the gait phase.

An eloquence of this orthopedic device is that the strap automatically spirals around the leg when the user holds the clip, moves it around the leg, and engages the receptacle. Both the suspension segment and the spiral segment concurrently position themselves without any user intervention.

The strap 18 is preferably not intended to be removed from the brace 10. However, if it is removed, certain color coding and instructions can be used to provide guidance to the user regarding reapplying the strap 18 to the brace 10.

Figure 16A:
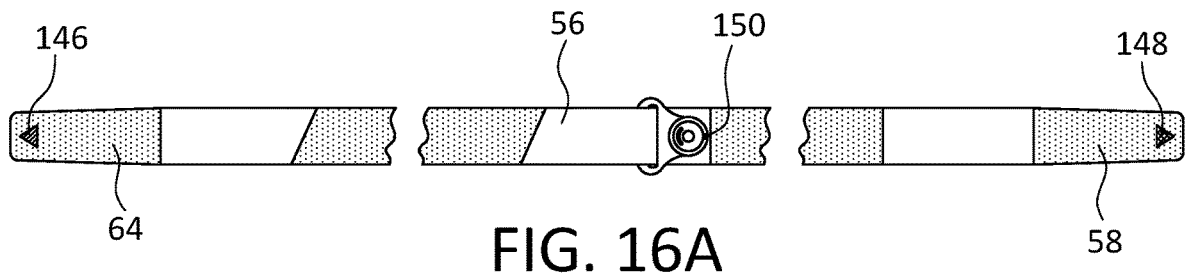
FIGS. 16A-16E show use of color codes to provide ease in applying the strap.

As can be seen in FIGS. 16A-16E, the strap 18 can be easily applied to the brace by use of color coding. In one embodiment three colors—yellow, blue, and orange can be used. The steps can be as follows: Referring to FIG. 16A, first, lay out the strap 18 flat with thigh hook sub-segment 64 (yellow arrow 146) and calf hook sub-segment 58 (blue arrow 148) hooks facing upwards. The color tags at both ends of the strap will be visible. This is useful for ensuring the proper installation of the strap.

Figure 16B:
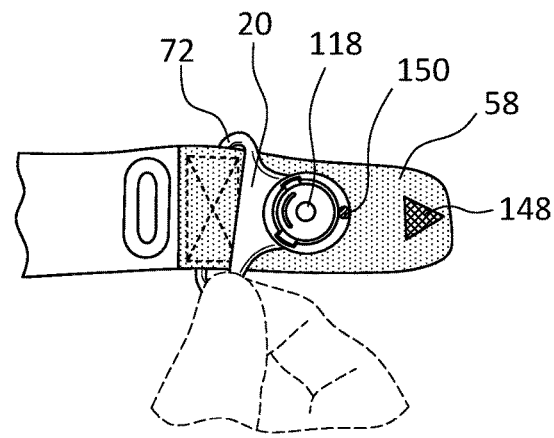

Referring to FIG. 16B, orient the clip 20 (orange dot 150) with color tag visible. Slide the D-ring portion 72 of the clip 20 over the calf end segment 44 (i.e. the calf hook sub-segment 58 with blue arrow 148). Button 118 of the clip is visible and facing the open end of the strap. Draw the clip 20 to the intermediate segment 56 of the strap.

Figure 16C:
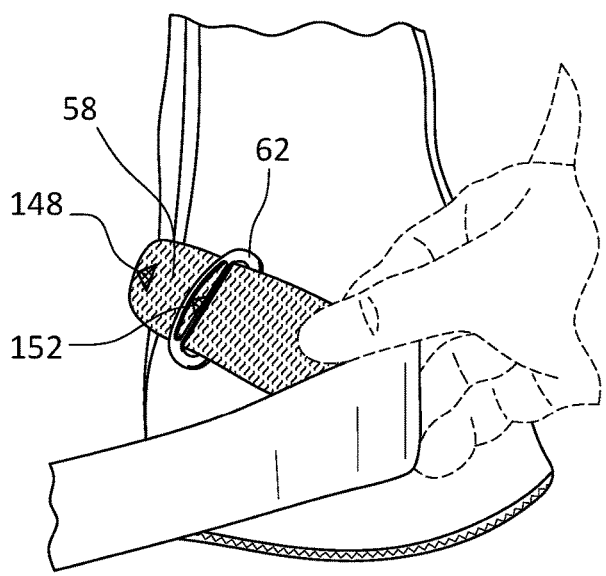

Referring to FIG. 16C, flip the strap 18 over. With calf hook sub-segment 58 (with blue arrow 148) facing downward, feed the strap over and thru the top of the calf D-ring 62 (with a blue arrow 152) until the strap stopper 65 passes thru the D-ring 62. The arrow directions establish proper orientation. Secure the calf hook sub-segment 58 to the calf loop sub-segment 60 located on the underside of the strap.

Figure 16D:
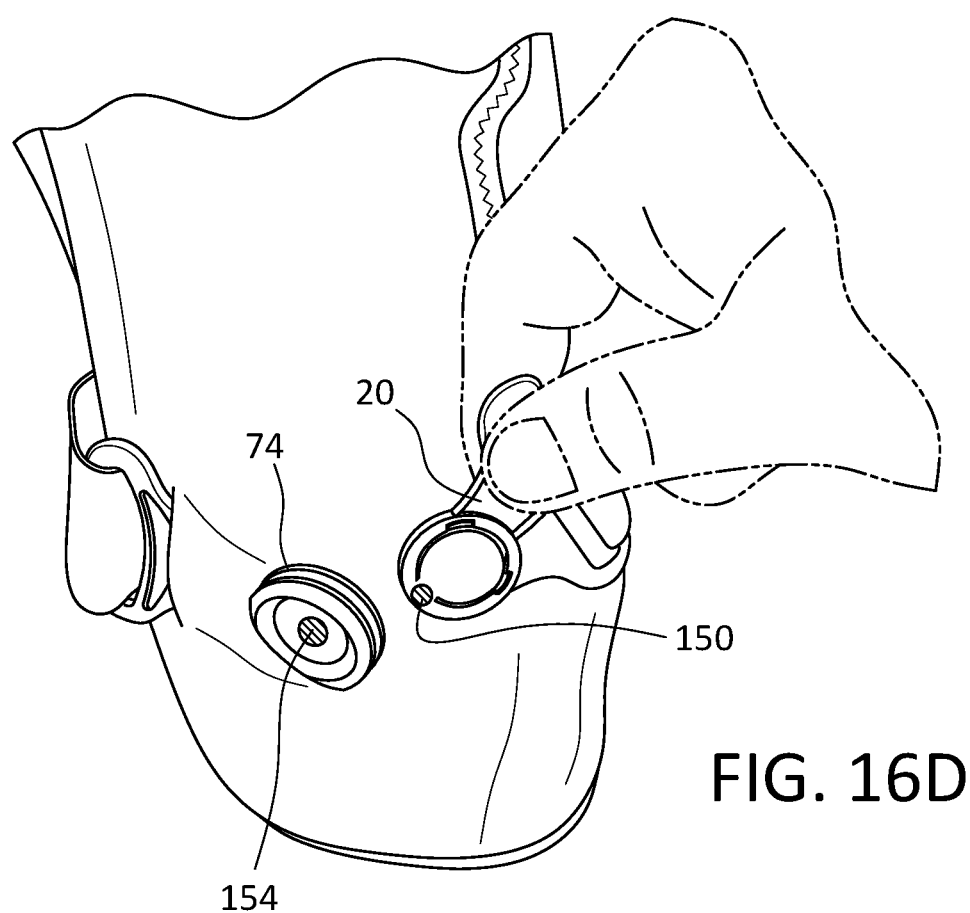

Wrap the strap 18 across the front of the brace and continue around the back. Referring to FIG. 16D, engage the clip 20 (with orange dot 150) into the clip receptacle 74 (with an orange dot 154).

Figure 16E:
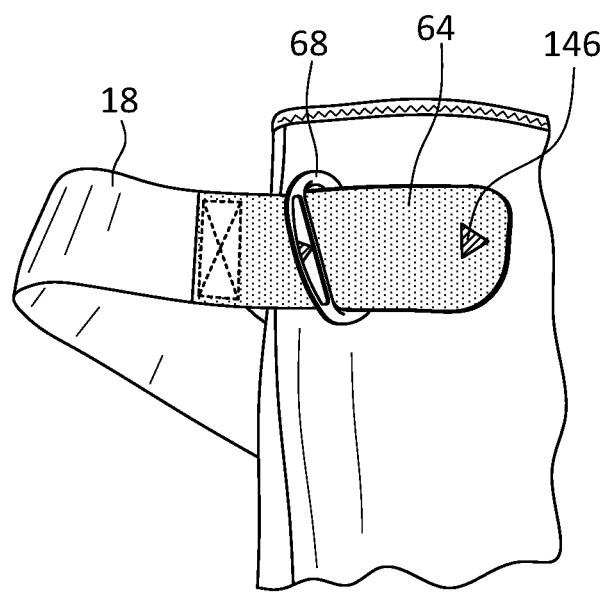

Referring to FIG. 16E, wrap the strap 18 around the back of the brace and continue around the front. Feed the thigh hook sub-segment 64 (with yellow arrow 146) of the strap thru the underside of the thigh D-ring 68 (yellow). Secure the strap end to the thigh loop sub-segment 66 of the strap.

As mentioned above, other embodiments and configurations may be devised without departing from the spirit of the invention and the scope of the appended claims.

The invention claimed is:

1. An orthopedic device, comprising:
   a) a wrap;
   b) an articulating frame housed within said wrap, comprising:
      i. a thigh portion including a semi-flexible curved thigh cuff;
      ii. a calf portion including a semi-flexible curved calf cuff; and,
      iii. a center hinge connecting said thigh portion and said calf portion;
   c) a strap attached to said articulating frame, wherein said strap includes:
      i. a calf end segment securely attachable to said calf portion of the articulating frame;
      ii. a suspension segment adjacent to said calf end segment;
      iii. a thigh end segment securely attachable to said thigh portion of the articulating frame;
      iv. a spiraling segment adjacent to said thigh end segment;
      v. an intermediate segment between said suspension segment and said spiraling segment, said intermediate segment formed of webbing material; and,
   d) a clip including a D-ring portion for engaging said intermediate segment, wherein said clip is engageable with a clip receptacle positioned on the calf portion of the articulating frame,
   wherein during use the suspension segment is configured to lay across a top part of a calf muscle to provide vertical support to minimize migration of the orthopedic device; and, the intermediate segment facilitates movement of the strap through the D-ring portion to provide adjustment of the spiraling segment and the suspension segment.

2. The orthopedic device of claim 1, wherein said clip includes a pushbutton portion; and, wherein said calf cuff includes a pivotal pushbutton receptacle secured thereto.

3. The orthopedic device of claim 2, wherein said pivotal pushbutton receptacle includes a protective raised rim, and wherein said pushbutton portion of the clip is concave.

4. The orthopedic device of claim 1, wherein said wrap, comprises:
   a) a main panel, configured to form a pocket for the articulating frame;
   b) a posterior panel secured to a first end of the main panel;
   c) a front thigh closure connected to a second end of the main panel, said front thigh closure including a thigh loop surface;

d) a front calf closure connected to said second end of the main panel, said front calf closure including a calf loop surface;
e) a thigh fastening tab extending from said posterior panel including a thigh hook material;
f) a calf fastening tab extending from said posterior panel including a calf hook material.

5. The orthopedic device of claim 4, wherein said posterior panel comprises three pieces configured for shaping the orthopedic device to a user's anatomy.

6. The orthopedic device of claim 1, wherein:
a) said calf end segment comprises a calf hook sub-segment spaced from a calf loop sub-segment, and wherein said calf portion of the articulating frame includes a calf D-ring configured to adjustably engage the calf hook sub-segment and said calf loop sub-segment; and,
b) said thigh end segment comprises a thigh hook sub-segment spaced from a thigh loop sub-segment, and wherein said thigh portion of the articulating frame includes a thigh D-ring configured to adjustably engage the thigh hook sub-segment and said thigh loop sub-segment.

7. The orthopedic device of claim 1, wherein said semi-flexible curved thigh cuff has a teardrop shape; and wherein said semi-flexible curved calf cuff has an upside-down teardrop shape.

8. The orthopedic device of claim 1, wherein said semi-flexible curved thigh cuff has a teardrop shape; said semi-flexible curved calf cuff has an upside-down teardrop shape; and, said teardrop shapes are defined by a series of positive curves from a wide end inflecting to a negative curve approaching a narrow end.

9. The orthopedic device of claim 1, wherein:
a) said thigh portion includes an upright thigh bar having an upright thigh bar first end and an upright thigh bar second end, said upright thigh bar first end being connected to said center hinge, wherein said semi-flexible curved thigh cuff includes a thigh cuff pocket for securing said upright thigh bar second end therewithin; and,
b) said calf portion includes an upright calf bar having an upright calf bar first end and an upright calf bar second end, said upright calf bar first end being connected to said center hinge, wherein said semi-flexible curved calf cuff includes a calf cuff pocket for securing said upright calf bar second end therewithin.

10. The orthopedic device of claim 1, wherein:
a) said thigh cuff comprises a first thigh side and a second thigh side, the first thigh side and the second thigh side being symmetrical about a central axis and being configured to wrap partially anteriorly and partially posteriorly to a leg; and,
b) said calf cuff comprises a first calf side and a second calf side, the first calf side and the second calf side being symmetrical about a central axis configured to wrap partially anteriorly and partially posteriorly to the leg.

11. The orthopedic device of claim 1, wherein:
a) said thigh cuff comprises a first thigh side and a second thigh side, the first thigh side and the second thigh side positioned about a central axis and being configured to wrap partially anteriorly and partially posteriorly to a leg; and,
b) said calf cuff comprises a first calf side and a second calf side, the first calf side and the second calf side positioned about a central axis configured to wrap partially anteriorly and partially posteriorly to the leg.

12. The orthopedic device of claim 1, wherein said strap comprises color coding thereon for providing guidance to a user regarding reapplying the strap if removed.

13. A method for donning an orthopedic device, comprising the steps of:
a) providing the orthopedic device, comprising:
i. a wrap;
ii. an articulating frame housed within said wrap, comprising:
a. a thigh portion including a semi-flexible curved thigh cuff;
b. a calf portion including a semi-flexible curved calf cuff; and,
c. a center hinge connecting said thigh portion and said calf portion;
iii. a strap attached to said articulating frame, wherein said strap includes:
a. a calf end segment securely attached to said calf portion of the articulating frame;
b. a suspension segment adjacent to said calf end segment;
c. a thigh end segment securely attached to said thigh portion of the articulating frame;
d. a spiraling segment adjacent to said thigh end segment;
e. an intermediate segment between said suspension segment and said spiraling segment, said intermediate segment formed of webbing material; and,
iv. a clip including a D-ring portion for engaging said intermediate segment, wherein said clip is engageable with a clip receptacle positioned on the calf portion of the articulating frame;
b) placing the orthopedic device around a leg of a user;
c) fitting the wrap around the leg of the user;
d) wrapping the strap from a side of the leg, across a front of the leg, continuing posteriorly across an upper portion of a calf, wherein the spiraling segment begins at the calf and spirals posteriorly and ends anteriorly at a thigh;
e) engaging the clip into the clip receptacle; and,
f) adjusting a strap tension at the thigh end segment.

14. The method of claim 13, including reapplying the strap if removed, wherein said strap comprises color coding thereon for providing guidance to the user regarding reapplying the strap.

* * * * *